United States Patent
Kelly et al.

(10) Patent No.: US 6,455,032 B1
(45) Date of Patent: Sep. 24, 2002

(54) COMPOSITION AND METHOD FOR PROTECTING SKIN FROM UV INDUCED IMMUNOSUPPRESSION AND SKIN DAMAGE

(75) Inventors: Graham Edmund Kelly, Northbridge; Alan James Husband, McMahon's Point, both of (AU)

(73) Assignee: Novogen Research Pty. Ltd. (AU)

( * ) Notice: Subject to any disclaimer, the term of this patent is extended or adjusted under 35 U.S.C. 154(b) by 0 days.

(21) Appl. No.: 09/582,317

(22) PCT Filed: Dec. 21, 1998

(86) PCT No.: PCT/AU98/01054

§ 371 (c)(1),
(2), (4) Date: Sep. 19, 2000

(87) PCT Pub. No.: WO99/36050

PCT Pub. Date: Jul. 22, 1999

(30) Foreign Application Priority Data

Dec. 24, 1997 (AU) .................................. PP1124

(51) Int. Cl.[7] .......................... A61K 7/42; A61K 7/44; A61K 7/00; A61K 31/44; A61K 31/405; A61K 31/35; A61K 31/12

(52) U.S. Cl. .......................... 424/59; 424/60; 424/400; 424/401; 514/294; 514/415; 514/456; 514/457; 514/685

(58) Field of Search .......................... 424/59, 60, 400, 424/401; 514/294, 415, 456, 457, 685

(56) References Cited

FOREIGN PATENT DOCUMENTS

| WO | WO 97/46208 | 12/1997 |
| WO | WO 98/08503 | 3/1998 |

OTHER PUBLICATIONS

Boyle et al., "Cancer, Warts and Sunshine in Renal Transplant Patient", The Lancet, Mar. 31, 1984, pp. 702–705.
Kinlen et al., "Collaborative United Kingdom—Australasian Study of Cancer in Patients Treated With Immunosuppressive Drugs", Br. Med. J., Dec. 8, 1979, pp. 1461–1466.
O'Dell et al., "Diminished Immune Response in Sun–Damaged Skin", Arch. Dermatol., May 1980, vol. 116, pp. 559–561.
Yoshikawa et al., "Susceptibility to Effects of UVB Radiation on Induction of Contact Hypersensitivity as a Risk Factor for Skin Cancer in Humans", J. Invest. Dermatol., Nov. 1990, vol. 95, pp. 530–536.
Ullrich, "Does Exposure to UV Radiation Induce a Shift to a Th–2–like Immune Reaction?", Photochem. Photobiol., Mar. 1996, vol. 64, pp. 254–258.
Brown, "Introduction to Organic Chemistry", 4th Edition, (Table of Contents), Brooks/Cole Publishing Co., Pacific Grove, CA, 1988.
Balsam et al., "Cosmetic Science and Technology", 2nd Edition, vols. 1 and 2 (Table of Contents), Wiley–Interscience, New York, 1972.
Flick, "Cosmetic and Toiletry Formulations", (Table of Contents) Noyes Publications, Park Ridge, N.J., 1984.
Flick, "Cosmetric and Toiletry Formulations", 2nd Edition, (Table of Contents), Noyes Publications, Park Ridge, N.J., 1989.
Jaonnou et al., "A Urinary Profile Study of Dietary Phytoestrogens. The Identification and Mode of Metabolism of New Isoflavonoids", J. Steroid. Biochem. Molec. Biol., vol. 54, pp. 167–184, 1995.
Kondo et al., "Interleukin–10 Inhibits the Elicitation Phase of Allergic Contact Hypersensitivity", J. Invest. Dermatol. vol. 103, pp. 811–814.
Reeve et al., "Dependence of Photocarcinogenesis and Photoimmunosuppression in the Hairless Mouse on Dietary Polyunsaturated Fat", Cancer letters, vol. 108, pp. 271–279, 1994.
Reeve et al., "Differential Photoimmunoprotection by Sunscreen Ingredients Is Unrelated to Epidermal cis Urocanic Acid Formation in Hairless Mice", J. Invest. Dermatol., vol. 103, pp. 801–806, 1994.
Canfield et al., "Characterization of UV Induced Keratoacanthoma–Like Lesions in HRA/Skh–1 Mice and Their Comparsion With Keratoacanthomas in Man", Pathology, vol. 17, pp. 613–616, 1985.
Reeve et al., "Carnosine (β–alanylhistidine) Protects From the Suppression of Contact Hypersensitivity by Ultraviolet B (280–320 nm) Radiation or by cis Urocanic Acid", Immunology, vol. 78, pp. 99–104, 1993.
Asherson et al., "Contact and Delayed Hypersensitivity in the Mouse", Immunology, vol. 15, pp. 405–416, 1968.

Primary Examiner—Shelley A. Dodson
(74) Attorney, Agent, or Firm—Finnegan, Henderson, Farabow, Garrett & Dunner L.L.P.

(57) ABSTRACT

Compositions and a method of protecting skin from either UV-induced immunosuppression or from UV-induced skin damage using a composition containing an extract of soy or clover, and/or the isoflavone compounds genistein, biochanin, dihydro-diadzein, formonentin, dihydrogeneistein, 2-dehydro-O-desmethyl-angolensin, tetrahydrodaidzein, equol, dehydro-equol, O-desmethyl-angolensin, or 6-hydroxy-O-desmethyl-angolensin.

21 Claims, No Drawings

COMPOSITION AND METHOD FOR PROTECTING SKIN FROM UV INDUCED IMMUNOSUPPRESSION AND SKIN DAMAGE

This invention relates in one aspect to compositions which are applied to the skin after ultra violet (UV) radiation exposure, particularly following exposure to the sun. Such compositions may be referred to as after-sun compositions. In another aspect the invention relates to compositions for oral administration which protect against UV induced skin damage. In another aspect the invention relates to methods for protecting the skin from UV induced immunosuppression and UV induced skin damage, such as that resulting from exposure to the sun.

Exposure of the skin to ultraviolet radiation causes both critical damage to the epidermal DNA, which may have long-term irreversible consequences if remaining unrepaired, and may lead to a specific impairment of the T lymphocyte immune system.

In chronically UV-exposed skin, damage to DNA culminates in carcinogenesis, the most common tumour in man being the basal cell carcinoma (BCC), followed by squamous cell carcinoma (SCC), and more rarely malignant melanoma. For example, approximately two-thirds of the Australian population suffer from non-melanoma skin cancer at some time in their lives, the proportion increasing with decreasing latitude, and leading the world. Australia also has the world's highest incidence of melanoma.

The immuosuppression caused by UV exposure appears to be a prerequisite for non-melanoma and melanoma cancer promotion. It is mediated by a number of mechanisms, such as the formation of epidermal cis-urocanic acid in UV-irradiated skin, the persistence of pyrimidine dimers in epidermal DNA, and the upregulation of inflammatory eicosanoids like PGE2. It is understood that photoimmunosuppression permits the initiated tumour cell to evade recognition and rejection by normal immunological mechanisms, to remain latent for extended periods, and to eventually proliferate into a tumour.

Immunocompromised patients, whether genetically (xeroderma pigmentosum) or pharmacologically (organ transplant recipients) [see Boyle et al (1984) *Lancet*, 31 March, 702–705 and Kinlen et al (1994) Invest Dermatol, *Br. J. Med.* ii 1461–1466], have a higher incidence of skin cancer. Also sun-exposed skin areas on humans are immunologically impaired compared with non-exposed skin [O'Dell et al (1980) *Arch. Dermatol.*, 116, 559–561], and the level of immunological responsiveness of skin cancer patients is reduced compared with non-skin cancer patients [Yoshikawa et al, *Invest. Dermatol.*, 95:530–536 (1990)]. The immune deficiency following UV exposure is now known to result from a deficiency in Th1 cell activity, whereas Th2 responses remain active [Ullrich, S. E. (1996) *Photochem. Photobiol.* 64, 254–258].

The chronic exposure of the skin to solar radiation is well documented as the cause of the photoageing phenomenon, such as thickening of skin, drying of skin, increased skin pigmentation, skin spots and skin lesions.

UV exposure, such as chronic solar UV radiation causes the well known effects of reddening of the skin with accompanying inflammation, known as erythema. This is often referred to as "sunburn" which is painful, often itchy, and generally results in a subsequent peeling of the skin which has been subject to chronic solar irradiation.

Erythema is particularly prevalent in light skinned individuals and children. Chronic erythema may predispose individuals to skin disorders, such as skin cancers in later life. Depending on an individual's skin colouration, erythema may result in as little as 20 minutes exposure to the sun.

With an increasing awareness of the dangers of UV exposure to skin, "sun blocks" or sunscreens have been available for a number of years. Sunscreens are applied to the skin prior to sun exposure. Typically sunscreen compositions contain UVA-type sunscreen agents and/or UVB-type sunscreen agents. Typical UVA-type sunscreen agents include certain benzophenones and dibenzylmethanes. Typical UVB-type sunscreen agents include substituted para-aminobenzoates, alkyl esters of para-methoxycinnamate and/or various esters of salicylic acid. Generally sunscreening agents are used in amounts effective to provide the desired level of protection from erythema caused by UVA and/or UVB radiation. Examples of many known sun screening agents are described in WO 96/14826 which is incorporated herein by reference.

Sun screening compositions may contain physical sun screening agents such as red petrolatum, or titanium dioxide, such as in amounts from 2–5% by weight of the total composition. Precipitated silica, kaolin, talc, chalk and the like may also be used in such compositions.

A diverse range of compounds have been proposed as UV absorbers for use in sunscreen compositions. Amongst this enormous class of sunscreen agents flavonoid compounds, including isoflavone compounds, have been mentioned. The applicant's investigations indicate that isoflavone compounds show poor UV absorbing capacity, contributing as little as 1.5 units sun protection factor (SPF) to sunscreen compositions.

Concerns have arisen with regard to the light stability of various UV absorbers, potential toxic effects of compounds over long term exposure, complexity and cost of formulations, and overall effectiveness of sunscreen compositions. Sunscreen compositions require specific application to the skin prior to UV exposure. Failure to apply sunscreen, inadequate application to the skin, and/or loss of sunscreen from the skin all have the potential to lead to UV damage to the skin.

Currently available sunscreens are not all efficacious in protecting skin from UV exposure, such that immune deficiency of skin and the potentially serious consequences which may ensue remain unaddressed.

It has surprisingly been found by the applicant that certain isoflavone compounds when applied to the skin subsequent to UV exposure or for oral administration prior to or following UV exposure, in the form of an after-sun composition, protect the skin from UV induced immunosuppression and UV induced skin damage. It has also been found that extracts of soy and clover protect skin from UV induced immunosuppression and UV induced skin damage.

In accordance with one aspect of the present invention there is provided a composition for application to the skin following UV exposure or for oral administration prior to or following UV exposure, which composition comprises a compound of the general Formula (I)

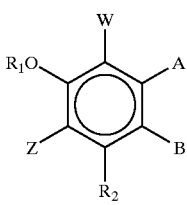

(I)

in which

Z is H, $R_1$ is H, or $R_ACO$ where $R_A$ is $C_{1-10}$ alkyl or an amino acid, $R_2$ is H, OH, or $OR_B$ where $R_B$ is an amino acid or $COR_A$ where $R_A$ is as previously defined, W is H, A is H or OH, and B is selected from

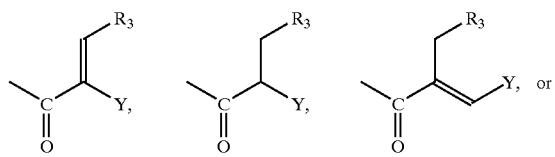

W is H, and A and B taken together form a six membered ring selected from

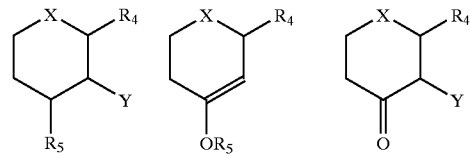

W, A and B taken with the groups with which they are associated comprise

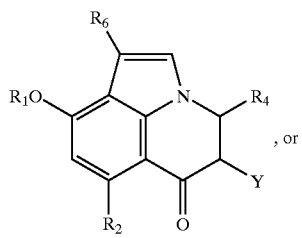

W and A taken together with the groups with which they are associated comprise

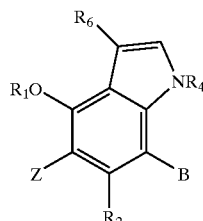

and B is

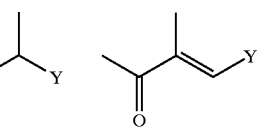

wherein $R_3$ is H, $COR_A$ where $R_A$ is as previously defined, $CO_2R_C$ where $R_C$ is $C_{1-10}$ alkyl, or $COR_B$ where $R_B$ is as previously defined, $R_4$ is H, $COR_D$ where $R_D$ is H, OH, $C_{1-10}$ alkyl or an amino acid, $CO_2R_C$ where $R_C$ is as previously defined, $COR_E$ where $R_E$ is H, $C_{1-10}$ alkyl or an amino acid, COOH, $COR_C$ where $R_C$ is as previously defined, or $CONHR_E$ where $R_E$ is as previously defined, $R_5$ is H, $CO_2R_C$ where $R_C$ is as previously defined, or $COR_COR_E$ where $R_C$ and R are as previously defined, and where the two $R_5$ groups are attached to the same group they are the same or different, $R_6$ is H or hydroxy $C_{1-10}$ alkyl, X is preferably O, but may be N or S, and Y is

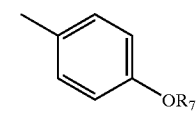

where $R_7$ is H, or $C_{1-10}$ alkyl, in association with a dermatologically acceptable or pharmaceutically acceptable carrier.

Preferably the compounds of the Formula (I) are selected from:

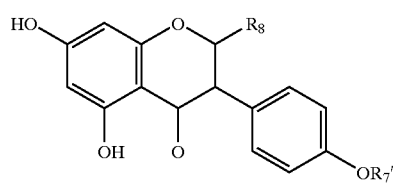

(1)

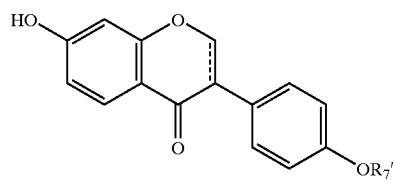

(2)

-continued
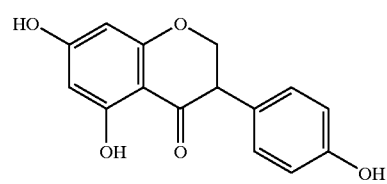
(3)
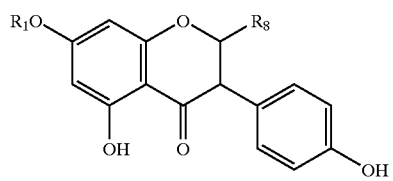
(4)
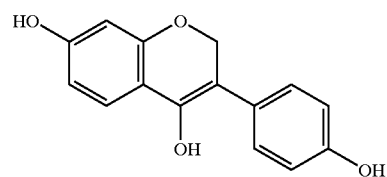
(5)
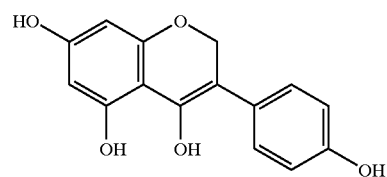
(6)
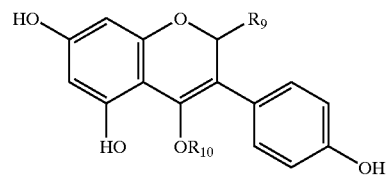
(7)
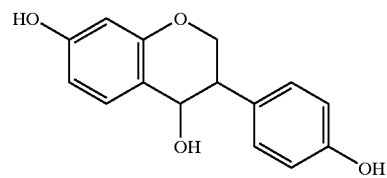
(8)
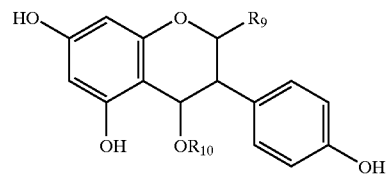
(9)
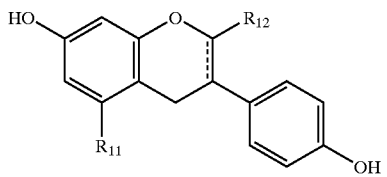
(10)
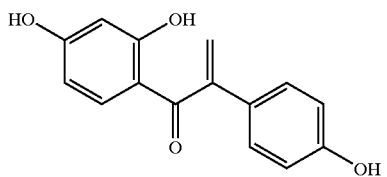
(11)
-continued
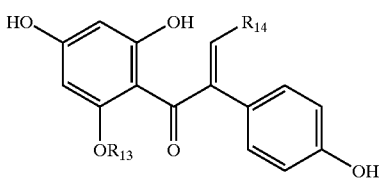
(12)
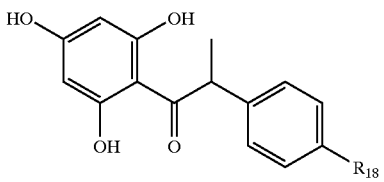
(14)
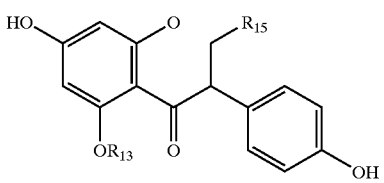
(15)
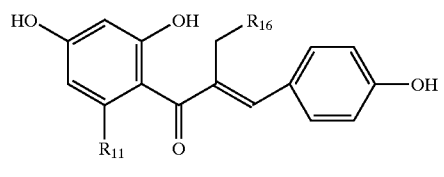
(16)
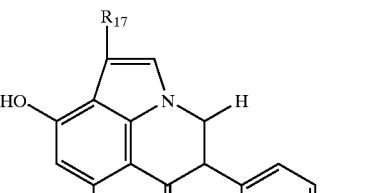
(17)
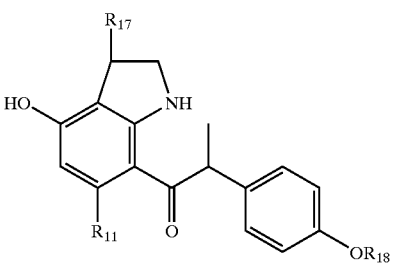
(18)
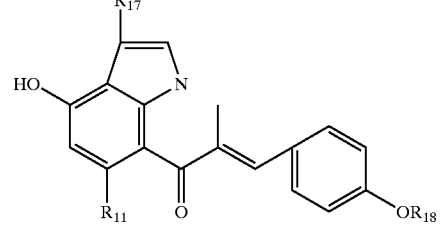
(19)
wherein
$R_{7'}$ is H or $CH_3$
$R_8$ is COR where $R_D$ is as previously defined, or H,
$R_9$ $CO_2R_C$ or $COR_E$ where $R_C$ and $R_E$ are as previously defined, $R_{10}$ is $COR_C$ or $COR_COR_E$ where $R_C$ and $R_E$ are as previously defined, $R_{11}$ is H or OH, $R_{12}$ is H, COOH, $CO_2R_C$ where $R_C$ and is as previously defined, or $CONHR_E$ where $R_E$ is as previously defined, $R_{13}$ is OH, $OR_B$ where $R_B$ is as previously defined, or $COR_A$ where $R_A$ is as previously defined, $R_{14}$ is H, or $COR_A$ where $R_A$ is as previously defined, $R_{15}$ is $COR_A$ where $R_A$ is as previously defined, $R_{16}$ is H, $COR_B$ or $CO_2R_C$ where $R_B$ and $R_C$ are as previously defined, $R_{17}$ is H or hydroxy $C_{1-10}$ alkyl, $R_{18}$ is H or $C_{1-10}$ alkyl, and === represents either a single bond or a double bond.

Alkyl groups may be straight or branched chains. $C_{1-10}$ alkyl preferably contains from 1 to 5 carbons, more preferably methyl, ethyl or propyl.

Certain of the above compounds may be referred to by the names genistein (compound 1 where $R_{7'}$ is H and $R_8$ is H), biochanin (compound 1 where $R_{7'}$ is $CH_3$ and $R_8$ is H), dihydrodaidzein (compound 2 where === is a bond and $R_{7'}$ is H), diadzein (compound 2 === is a double bond and $R_{7'}$ is H) formonentin (compound 2 where === is a double bond and $R_{7'}$ is $CH_3$), dihydrogeneistein (compound 5 in the keto form), 2-dehydro-O-desmethyl-angolensin (compound 11), tetrahydrodaidzein (compound 8), equol (compound 10 when === is a single bond), dehydroequol (compound 10 where === is a double bond), O-desmethyl-angolensin (ODMA—compound 13), and 6-hydroxy-O-desmethylangolensin (6-hydroxy-ODMA—compound 14).

Compounds of the Formula (I) include isomers, keto-enol tautomers, and physiologically acceptable salts. Isomeric forms, keto-enol forms, and salts can be prepared according to methods well known in the art, such as described by Brown, W. H., *Introduction to Organic Chemistry*, 4th Edition, Brooks/Cole Pub. Co., California, (1988).

In another aspect this invention is concerned with compositions containing an extract of soy and/or clover in association with a dermatologically acceptable carrier.

The compositions of the present invention do not include a UV absorber or a plurality of UV absorbers added for the purpose of protecting against UV irradiation. Nor do the compositions of this invention include any stabilizing compounds which provide UV stability or other stability to UV absorbing compounds given the absence of such compounds from the compositions of the present invention.

Dermatologically acceptable carriers are those which are compatible with the skin and can be readily applied to the skin by standard means. Components of such carriers include, but are not limited to, one or more of water, glycerol, alcohol, propylene glycol, fatty alcohols, triglycerides, fatty acid esters, and mineral oils. Dermatologically acceptable carriers may be in the form of lotions, creams, gels, mousses, aqueous liquids of varying viscosity, waxed based sticks, aerosols, alcohol sticks and the like. Examples of formulations well known in the art may be found in Balsam, M. S. and Sagrin, E. (editors) *Cosmetic Science and Technology*, second edition, Volume 1 and 2, Wiley-Interscience, a division of John Wiley & Sons Inc, New York, 1972 and Flick, E. W. *Cosmetic and Toiletry Formulations*, Noyse Publications 1984, each of which is incorporated herein by reference.

Dermatologically acceptable carriers may include one or more emollients, emulsifiers, surfactants, waxes, thickeners, film formers, preservatives and perfumes. Such agents are well known in the art, and are described in *Cosmetic Science and Technology and Cosmetic and Toiletry Formulations* referred to above. Further examples of such additional components are provided for example in WO96/14826.

An example of the standard lotion for topical application to the skin contains the following:

| paraffin oil | bees wax | triethanolamine |
| olive oil | glyceryl monostearate | |
| anhydrous lanolin | oleic acid | |
| stearic acid | water | |

The components listed above, other than water, may be present in an amount from about 0.01% to 10% w/w. Water may be present in an amount from about 20% to about 90% w/w. Compounds of the Formula (I) may be present in such a lotion in an amount from 0.05% to 10% w/w.

Compositions according to the present invention may be readily prepared according to standard procedures known in the art for the preparation of compositions for topical application to the skin, for example as described by Balsam, M. S. and Sagrin, E. (editors) *Cosmetic Science and Technology*, second edition, Volume 1 and 2, Wiley-Interscience, a division of John Wiley & Sons Inc, New York, 1972 and Flick, E. W. *Cosmetic and Toiletry Formulations*, Noyse Publications, 1984. By way of example, compositions may be prepared by blending together the compounds of the Formula (I) (optionally dissolved in a solvent such as DMSO, ethanol, paraffin oil, olive oil or other suitable solvents) and one or more dermatological acceptable carriers, such as first by dissolving.

Pharmaceutically acceptable carriers and dosage forms for oral administration are well known in the art, and are described for example in Remingtons Pharmaceutical Sciences, Mack Publishing Co., Ed. Osol, 10th Edition. The carrier may be a solid or a liquid, or both and is preferably formulated with compounds of the formula (1) or extracts of soy or clover as a unit dose, for example, a tablet, which may contain from 0.5% to 60% by weight of the active component. One or more active compounds may be formulated with one or more carriers by well known techniques of pharmacy. Formulations may be prepared by uniformly and intimately admixing the active compound with a liquid or finely divided solid carrier or both, and then, if necessary, shaping the resulting mixture to form a unit dosage. Moulded tablets may, for example, be made by moulding together powdered components moistened with an inert liquid binder. Compositions may be administered before and/or after UV exposure. Conveniently compositions are administered daily, for example giving a daily administration of 0.05 mg to 500 mg per day of active components.

Compounds of the Formula (I) may be prepared according to procedures disclosed in PCT/AU97/00563 which is incorporated herein by reference. Compounds of the Formula (I) may be purified from human urine according to the procedures of Jaonnou et al (1995) *J. Steroid. Biochem. Molec. Biol.*, 54, 167–184 which is incorporated herein by reference.

Extracts of soy or clover may be prepared according to WO93/23069, the teachings of which are incorporated by reference. As described in WO93/23069 soy or clover may be extracted with a mixture of organic solvent (such as ethanol, chloroform, acetone, ethyl acetate and the like) and water. The ratio of solvent in water may be from 0.1% to 99.9%, preferably 40% to 60%.

Red clover (*T. pratense*) and subterranean clover (*T. subterranean*) are preferred clovers. Raw plant material may be dried, chaffed or otherwise comminuted and then subject to extraction. The resultant organic solvent layer following extraction is removed such as by distillation, and the aqueous layer and residual material from the organic layer concentrated as desired, such as by distillation. In respect of soy, beans may be treated to remove the hull (such as by using a tumble mill which splits the beans into two cotyledons and a hypocotyl which may be separated from one another). Cotyledons, and optionally hypocotyls, may be comminuted and then subject to extraction as described above. Extracts may include one or more compounds of the Formula (I).

Extracts are formulated with a dermatologically acceptable carrier as herein described to give a composition for application to the skin, or formulated for oral administration. Compositions may contain from 0.01% to 10% w/w of extract.

The composition of the present invention may include β-(1-3)(1,6)-glucan (such as prepared according to PCT/AU96/00138, the teachings of which are incorporated herein by reference), which may be present in an amount from 0.1% to 30% w/w. If particulate, the glucan may be dissolved in 0.1% DMSO or other suitable dissolving solvent. Such compositions may exhibit synergism between the respective components resulting in highly potent protection from UV induced skin damage. Accordingly, this invention in another aspect related to compositions and methods of treatment, as described herein, which include β-(1-3)(1,6)-glucan.

UV induced skin damage refers to any sunlight or other UV damage which effects skin, whether of a human or animal. Such damage includes erythema (reddening and swelling of the skin, often referred to as sunburn) photoaging of skin such as hyperkeratinization and elastosis and skin lesions such as precancerous and cancerous lesions, for example actinic keratoses and pre-malignant and malignant skin cancers.

According to another aspect of this invention there is provided a method for protecting skin from UV induced immunosuppression and UV induced skin damage which comprises applying to the skin of a subject after UV exposure a composition which comprises a compound of the Formula (1) as described in association with a dermatologically acceptable carrier. The composition may include β-(1,3)(1,6)-glucan.

In another aspect of this invention there is provided a method for protecting skin against UV induced immunosuppression and UV induced skin damage which comprises orally administering to a subject either before and/or after UV exposure a compound of the Formula (I) or an extract of soy or clover.

Compositions are applied to the skin following sun exposure, and are generally applied after each exposure to the skin, or alternatively at the end of a day following a series of exposure of the skin to sun.

Compositions may be applied to the skin by any convenient means known in the art, such as by way of being rubbed on, rolled on, sprayed on, wiped on or the like. The mode of application would generally depend upon the nature of the formulation, whether a cream, foam, lotion, roll-on "stick", liquid of varying viscosity, or the like.

Particularly preferred compounds of the Formula (I) for use in compositions and methods of the present invention are genistein (compound 1 where $R_{7'}$ is , and $R_8$ is H), equol (compound 10 where === is a bond) and dehydroequol (compound 10 where === is a double bond), tetrahydrodaidzein (compound 8) and O-desmethyl-angolensin (ODMA—compound 13).

In another aspect of this invention there is provided use of compounds of the Formula (I) or an isoflavone extract of soy or clover for the manufacture of a medicament for the treatment, amelioration, prophylaxis and/or prevention of UV induced immunosuppression in the skin, and UV induced skin damage.

In another aspect this invention is concerned with an article which includes a composition as herein defined. Examples of such articles include wipes having applied thereto the aforementioned compositions, emollient sticks, spray devices, containers or the like. O'Dell et al (1980 *Arch. Dermatol*, 116, 559–561) have shown that sun-exposed skin areas on humans are immunologically impaired according to non-exposed skin. A standard model for testing immunosuppression, that is a model with reference to human immunosuppression, is the hairless mouse. A standard test in the hairless mouse model is the contact hypersensitivity (CHS) reaction to an immune irritant such as oxazolone (Asherson and Ptak, *Immunology*, (1968) 15:405–416). The compound oxazolone induces a vigorous immune response in the hairless mouse which may be measured by ear swelling. Immune suppression by UV light or other agents can be readily tested in the model. See for example Kondo, S, McKenzie, R. C., Sauder, D. N., *J. Invest. Dermatol.*, 103:811–814; Reeve et al, *Cancer Letts.*, 108:271–279 (1996); and Reeve et al, *J. Invest. Dermatol.*, 103:801–806 (1994). As will be shown in the non-limiting examples which follow, compositions comprising compounds of the Formula (I) were active in the treatment/prevention/amelioration of UV induced immunosuppression in the hairless mouse model, which as discussed above is directly referable to the situation in human skin, for example, Yoshikawa et at, *J. Invest. Dermatol.*, 95:530–536, (1990).

Hairless mouse strains such as the HRA-Skh-1 mice are a standard mouse model used to study solar damage to human skin [Canfield et al, *Pathology*, 17:613–616, (1985)]. Exposure of the hairless mouse to UV light mimics "sunburn" in humans. With continued irradiation treatment, this on-going damage is reflected in progressive thickening of the skin which histologically mimics hyperkeratinization and elastosis associated with photoaging and chronically sun-exposed skin in humans. Pre-malignant tumours begin to appear with several weeks of completion of the ultra violet light regimen. Over an ensuing time period there is a progressive development of pre-malignant and malignant tumours, the histology and behaviour of which closely mimic actinic keratoses and pre-malignant and malignant skin cancers that develop in humans in response to sunlight.

It has been found by the inventors that compositions containing compounds of the Formula (I), or extracts as herein described, with or without β-(1,3)(1,6)-glucan when applied to the skin in a dermatologically acceptable carrier following ultra violet irradiation, or by oral administration before and/or after ultra violet irradiation, provides protection from UV induced skin damage such as erythema, photoaging effects (as evidenced by progressive thickening of the skin) and a development of other UV induced lesions of the skin including pre-malignant and malignant skin cancers.

This invention will now be described with reference to the following non-limiting examples which illustrate various embodiments of the invention.

EXAMPLE 1

Preparation of Lotions Containing Compositions of the Formula (I)

A lotion ("base or test lotion") was prepared by mixing together the following components:

| | ml | | ml |
|---|---|---|---|
| paraffin oil | 80 | glyceryl monostearate | 60 |
| olive oil | 60 | oleic acid | 25 |
| anhydrous lanolin | 60 | water | 1200 |
| stearic acid | 58 | triethanolamine | 27 |
| beeswax | 10 | | |

Compounds of the Formula (I) were dissolved in 0.1% dimethylsulfoxide (DMSO) and incorporated into the base lotion in an amount from 0.01% to 10% w/w.

Test lotion "A" was prepared containing 20 μM of various compounds of the Formula (I) dissolved in 0.1% DMSO (a primary solvent for the compounds). Test lotion 'B' was prepared containing 20 μM of various compounds of the Formula (I) dissolved in 0.1% DMSO in combination with a solution of β-(1,3)(1,6)-glucan (10% w/w).

An extract of red clover was prepared according to WO93/23069. The aqueous extract, or a particulate or dried extract dissolved in 0.1% DMSO is incorporated into the base lotion in an amount of 0.5% w/w.

EXAMPLE 2

UV Induced Immunosuppression

The CHS reaction in mice is a standard model for immunosuppression and is a representative model for human immunosuppression (Yoshikawa et al, *Invest. Dermatol.*, 95:530–536 (1990)).

The CHS reaction was carried out according to the protocol of Reeve et al, *Immunology*, 78:99–104 (1993). Hairless albino Sh:HR-1 mice were divided into two treatment groups. The first treatment group designated group 1 was not subject to UV irradiation, and received either 0.2 ml of test lotion "A" or test lotion 'B' painted on to the dorsal skin on four consecutive days (that is, 4 μmol/mouse, or approximately 0.1 μmol/cm$^2$). The second treatment group, group 2, were UV irradiated with a minimal erythemal dose of UV light which simulates the toxic effect of sunlight on the skin. After each daily UV treatment 0.2 ml of treatment solution was applied to the dorsal skin as for treatment group 1. Mid-dorsal skinfold thickness was measured every twenty four hours to indicate erythema oedema. CHS to oxazolone was induced on abdominal skin seven days after the first treatment followed by challenge on the ears on day 15, and average ear swelling was determined as a measure of immune response.

Genistein, daidzein, equol, tetrahydrodaidzein, ODMA, dehydroequol and clover extract were tested in this experiment in test lotion "A". Equol, genistein and clover extract were also tested in tes lotion 'B'. The results expressed below are given as a percentage of suppression of CHS measured with reference to the non-UV exposed treatment group 1, which is induced by UV exposure. Results are as follows:

| | % Suppression of CHS | |
|---|---|---|
| Hours of ear challenge | 18 | 21 |
| Base lotion | 24 | 37 |
| Genistein | 14 | 13 |
| Daidzein | 27 | 37 |
| Equol | 12 | 5 |
| tetrahydrodaidzein | 33 | 31 |
| dehydroequol | 10 | 4 |
| Clover extract | 8 | 9 |
| Genistein and glucan | 11 | 9 |
| Equol and glucan | 8 | 3 |
| Clover extract and glucan | 5 | 5 |

The above results clearly show that genistein, dehydroequol and equol have significant activity in prevention/amelioration of UV induced immunosuppression as does the clover extract. In contrast, the compounds daidzein and tetrahydrodaidzein did not ameliorate the effects of UV induced immunosuppression.

Erythema/oedema was measured at day four and day seven of the treatment groups. These results show that genistein and equol suppressed erythema/oedema. For example, at seven days after treatment for base lotion "A" average skin fold thickness was six units (that is 0.006 in), for the daidzein containing lotion average skin fold increase was seven units, and for tetrahydrodaidzein average skin fold thickness was five units. In contrast, for equol, genistein, dehydroequol and ODMA there was a negative average skin fold increase of approximately 0.2, which corresponds to substantially no increase in skin fold thickness. This result shows that compositions of the Formula (I) are effective in protecting against UV induced skin damage, particularly erythema, oedema, and thickening of the skin.

EXAMPLE 3

Tests were performed at the Australian Photobiology Testing Facility at the University of Sydney. Human subjects were tested in a controlled solarium. A grid was established using reference coordinate points on the back of each subject, thereby providing a series of treatment sites on the back of each patient where the erythema-reducing potential of compositions according to the invention could be tested.

Compounds of the Formula (I) were dissolved in DMSO and incorporated into base lotion "A" to contain 100 μM of active ingredient, and 0.5% DMSO.

Topical applications were made to the back of the patient within the treatment grid which was established to provide a series of sites for UV irradiation, and subsequent application of compositions. Topical application consisted of 2 mg/cm$^2$ lotion applied firmly, followed by a second 2 mg/cm$^2$ applied but not rubbed in. Each topical treatment was therefore 0.4 nmols/cm$^2$ compound in the Formula (I).

The treatment procedure was as follows. On the first day of treatment a minimum erythemal dose of UV (MED) was established for each subject, this being the minimum degree of UV light which on visual determination produces a reddening of the skin. From this data, which is specific for each patient, a 0.75 level of minimum erythema dose was calculated (0.75×MED). The first treatment day was a Monday. Subsequent treatments were as follows:

Tuesday
  Expose 3×3 skin sites to 0.75 MED UV.
  Immediately, at four hours and at six hours post-UV,
    1 apply nil to three sites
    2 apply topical base lotion to three sites 3 apply topical equol lotion to three sites according to technique above.

Wednesday

Assess erythema (none visible as expected).

Re-expose same 3×3 skin sites to 0.75 MED UV.

Immediately, at four hours and at six hours post-UV, apply topical lotions as above.

Thursday

Assess erythema visually by ranking the colour intensity of the 3×3 skin sites.

Re-expose same 3×3 skin sites to one MED UV.

Topical applications as before

Friday

Assess erythema.

The results showed a progressively more intense erythema development peaking at fifty five and a half hours which gradually faded. There was no statistical difference between erythema intensity at triplicate sites receiving UV alone, compared with sites receiving UV plus base lotion. There was a significant reduction in erythema intensity at sites receiving UV plus a lotion containing compounds of the Formula (I), compared with UV alone or base lotion plus UV. A representative result is presented below where the compound of the Formula (I) was equol.

Average erythema intensity (n=3)+/−SEM

| Time Point Hours | UV alone | UV + vehicle | UV + compound of Formula (I) | SEM UV alone | SEM + vehicle | SEM + compound of Formula (I) |
|---|---|---|---|---|---|---|
| 48 | 0.3 | 0.33 | 0.21 | 0.08 | 0.07 | 0.04 |
| 52 | 0.58 | 0.67 | 0.21 | 0.14 | 0.18 | 0.04 |
| 55.5 | 1.5 | 1.25 | 0.67 | 0.29 | 0.31 | 0.18 |
| 71 | 1 | 1.17 | 0.67 | 0 | 0.36 | 0.27 |
| 75 | 1 | 1.04 | 0.38 | 0 | 0.44 | 1 |
| 77 | 0.67 | 1.17 | 0.54 | 0.14 | 0.36 | 0.21 |

The above results are significant when tested by student's t-test at individual inspection times. These results demonstrate that compositions containing compounds of the Formula (I) can be used in therapeutic treatment to prevent UV damage after sun exposure in humans.

EXAMPLE 4

The CHS reaction was carried out as in Example 2. Hairless albino Sh:HR-1 mice were divided into eight treatment groups as shown:

1. base lotion+MED (UVB) for 3 days
2. glucan (20%) in base lotion+1 MED (UVB) for 3 days
3. Equol (2.5 uM) in base lotion+1 MED (UVB) for 3 days
4. Equol (2.5 uM)+glucan (20%) in base lotion+1 MED (UVB) for 3 days
5. base lotion and no irradiation for three days (Control)
6. glucan (20%) in base lotion and no irradiation for three days (Control)
7. Equol (2.5 uM) in base lotion and no irradiation for three days (Control)
8. Equol (2.5 uM)+glucan (20%) in base lotion and no irradiation for three days (Control)

On days 7 and 8 the mice were sensitised with 2% oxazolone in alcohol (100 Oul/mouse). On day 14, the ears were challenged with 2% oxazolone (20 ul/mouse). On day 15, the ears were measured for skin fold thickness and suppression of chronic hypersensitivity. The results indicated that both glucan and equol were effective in decreasing the percentage suppression of chronic hypersensitivity and skin fold thickness, and that in combination they provided potentiated protection when compared to the control groups.

| Lotion | % Suppression of CHS | Difference in skin fold thickness from day 1 (mm) |
|---|---|---|
| Base lotion only | 41% | 47.7 |
| Glucan only | 4.5% | 25 |
| Equol only | 6% | 29.8 |
| Glucan + equol | 2.5% | 16.8 |

EXAMPLE 5

Hairless albino Sh:HR-1 mice were divided into two groups each containing 20 animals. The first group receiving red clover extract diet (prepared as described in WO 93/23069), and the second control group receiving a phytoestrogen free diet. Both groups received 1 minimal erythemal does of UVB light to stimulate the toxic effect of sunlight on the skin daily for 10 weeks. At weeks 11, 13, 14, 15, 16 and 17 the number of skin tumours on each animal were measured and calculated as tumour multiplicity, i.e. average number of tumours per mouse. The results showed a significant protection ($p<0.05$) against UVB induced carcinogenesis in mice fed a red clover diet after 17 weeks.

| Time (weeks) From Initial UVB Irradiation | Tumour Multiplicity: Control | Tumour Multiplicity: Red Clover |
|---|---|---|
| 11 | 0 | 0 |
| 13 | 0.13 | 0.25 |
| 14 | 0.37 | 0.46 |
| 15 | 0.82 | 0.76 |
| 16 | 1.65 | 1.01 |
| 17 | 2.62 | 1.51 |

The same model is used with compositions containing compounds of the formula (I). Protection against UVB induced carcinogenesis is observed.

Throughout this pecification, unless the context requires otherwise, the word "comprise", or variation such as "comprises" or "comprising" or the term "includes" or variations thereof, will be understood to imply the inclusion of a stated element or integer or group of elements or integers but not the exclusion of any other element or integer or group of elements or integers. In this regard, in construing the claim scope, an embodiment where one or more features is added to any of claims is to be regarded as within the scope of the invention given that the essential features of the invention as claimed are included in such an embodiment.

All publications referred to herein are incorporated by reference.

What is claimed is:

1. A composition for application to the skin following UV exposure or for oral administration prior to or following UV exposure, which composition comprises a compound of the general Formula (I)

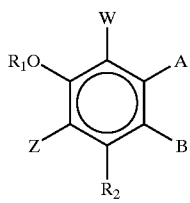

in which

Z is H,

R₁ is H, or R_ACO where R_A is C₁₋₁₀ alkyl or an amino acid,

R₂ is H, OH, or OR_B where R_B is an amino acid or COR_A where R_A is as previously defined, W is H, A is H or OH, and B is selected from

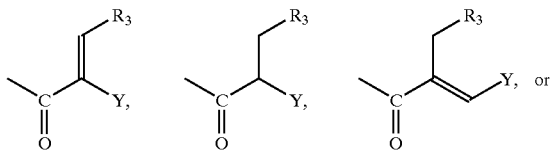

W is H, and A and B taken together form a six membered ring selected from

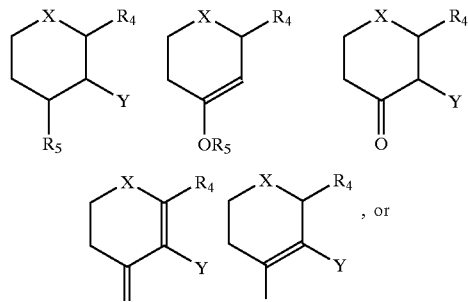

W, A and B taken with the groups with which they are associated comprise

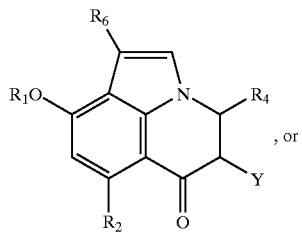

W and A taken together with the groups with which they are associated comprise

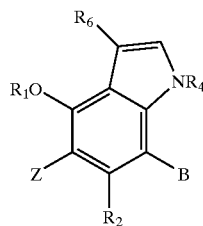

and B is

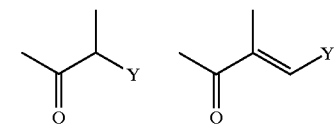

wherein

R₃ is H, COR_A where R_A is as previously defined, CO₂R_C where R_C is C₁₋₁₀ alkyl, or COR_B where R_B is as previously defined, R₄ is H, COR_D where R_D is H, OH, C₁₋₁₀ alkyl or an amino acid, CO₂R_C where R_C is as previously defined, COR_E where R_E is H, C₁₋₁₀ alkyl or an amino acid, COOH, COR_C where R_C is as previously defined, or CONHR_E where R_E is as previously defined, R₅ is H, CO₂R_C where R_C is as previously defined, or COR_COR_E where R_C and R are as previously defined, and where the two R₅ groups are attached to the same group they are the same or different, R₆ is H or hydroxy C₁₋₁₀ alkyl, X is preferably O, but may be N or S, and Y is

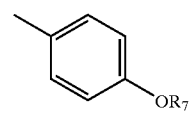

where

R₇ is H, or C₁₋₁₀ alkyl, in association with a dermatologically acceptable or pharmaceutically acceptable carrier.

2. A composition according to claim 1 wherein compounds of the Formula (I) are selected from:

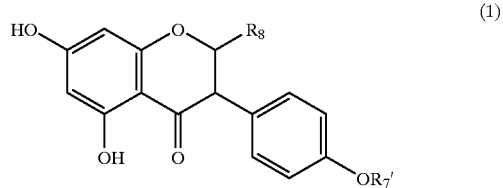

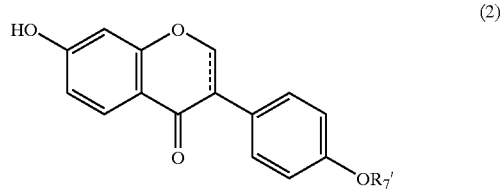

-continued
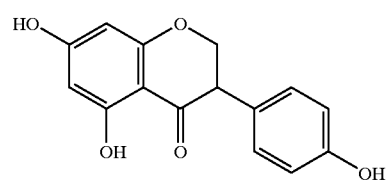
(3)
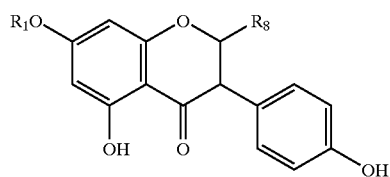
(4)
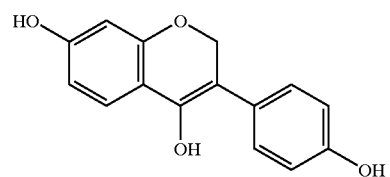
(5)
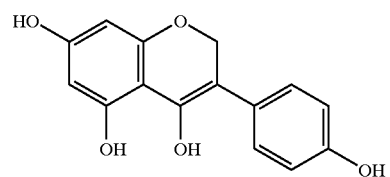
(6)
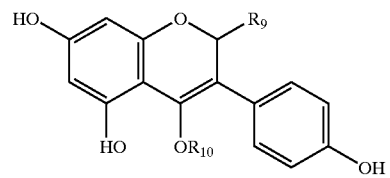
(7)
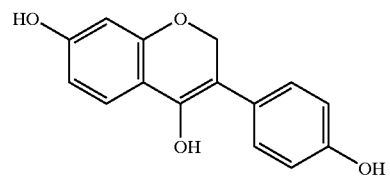
(8)
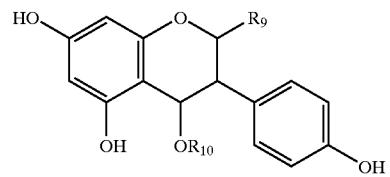
(9)
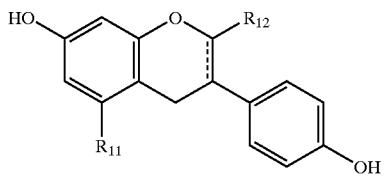
(10)
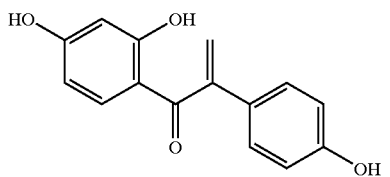
(11)
-continued
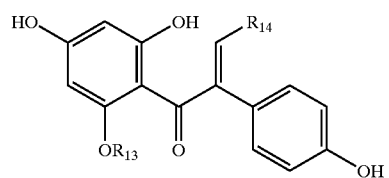
(12)
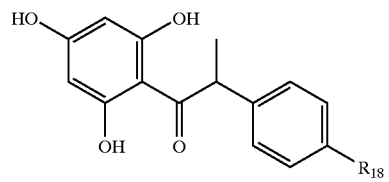
(14)
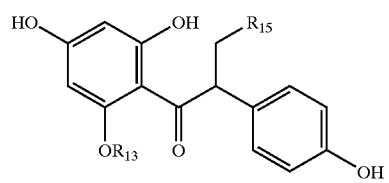
(15)
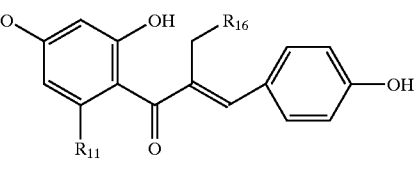
(16)
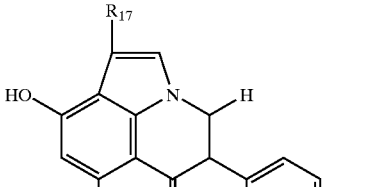
(17)
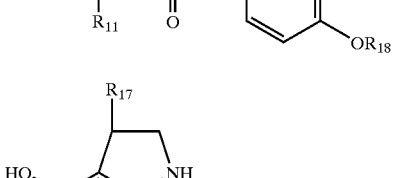
(18)
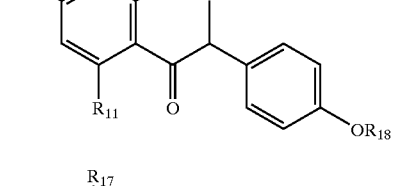
(19)
wherein
$R_{7'}$ is H or $CH_3$,
$R_8$ is COR where $R_D$ is as previously defined, or H,
$R_9$ $CO_2R_C$ or $COR_E$ where $R_C$ and $R_E$ are as previously defined, $R_{10}$ is $COR_C$ or $COR_COR_E$ where $R_C$ and $R_E$ are as previously defined, $R_{11}$ is H or OH, $R_{12}$ is H, COOH, $CO_2R_C$ where $R_C$ and is as previously defined, or $CONHR_E$ where $R_E$ is as previously defined, $R_{13}$ is OH, $OR_B$ where $R_B$ is as previously defined, or $COR_A$ where $R_A$ is as previously defined, $R_{14}$ is H, or $COR_A$ where $R_A$ is as previously defined, $R_{15}$ is $COR_A$ where $R_A$ is as previously defined, $R_{16}$ is H, $COR_B$ or $CO_2R_C$ where $R_B$ and $R_C$ are as previously defined, $R_{17}$ is H or hydroxy $C_{1-10}$ to alkyl, $R_{18}$ is H or $C_{1-10}$ alkyl, and "===" represents either a single bond or a double bond.

3. A method for protecting skin from UV induced immunosuppression and UV induced skin damage which comprises applying to the skin of a subject after UV exposure a composition which comprises a compound of the Formula (I) as defined in claim 1 or an extract of soy or clover, in association with a dermatologically acceptable carrier.

4. A method for protecting skin from UV induced immunosuppression and UV induced skin damage which comprises orally administering to a subject either before and/or after UV exposure a composition which comprises a compound of the Formula (I) as defined in claim 1 or an extract of soy or clover, in association with a pharmaceutically acceptable carrier.

5. A method according to claim 3 wherein the composition further comprises β-(1,3)(1,6)-glucan.

6. A composition for application to the skin following UV exposure, which composition comprises an extract of soy or clover in association with a dermatologically acceptable carrier.

7. A composition according to claim 1, further comprising β-(1,3)(1,6)-glucan.

8. A method for protecting skin from UV induced immunosuppression and UV induced skin damage which comprises applying to the skin of a subject after UV exposure, or orally before or after UV exposure, a composition as defined in claim 1.

9. A method of treating UV induced immunosuppression in the skin, comprising administering to a host at least one compound of formula (I) as defined in claim 1.

10. A method of treating UV induced skin disorders, comprising administering to a host at least one compound of formula (I) as defined in claim 1.

11. A method for prophylaxis and/or prevention of UV induced immunosuppression in the skin, comprising administering to a host at least one compound of formula (I) as defined in claim 1.

12. A method for prophylaxis and/or prevention of UV induced skin disorders, comprising administering to a host at least one compound of formula (I) as defined in claim 1.

13. A method according to claim 4 wherein the composition further comprises β-(1,3)(1,6)-glucan.

14. A composition according to claim 2 further comprising β-(1,3)(1,6)-glucan.

15. A composition according to claim 6 further comprising β-(1,3)(1,6)-glucan.

16. A method for protecting skin from UV induced immunosuppression and UV induced skin damage which comprises applying to the skin of a subject after UV exposure, or orally before or after UV exposure, a composition as defined in claim 2.

17. A method for protecting skin from UV induced immunosuppression and UV induced skin damage which comprises applying to the skin of a subject after UV exposure, or orally before or after UV exposure, a composition as defined in claim 6.

18. A method for protecting skin from UV induced immunosuppression and UV induced skin damage which comprises applying to the skin of a subject after UV exposure, or orally before or after UV exposure, a composition as defined in claim 7.

19. A composition according to claim 2 wherein the compounds of Formula (I) are genistein, equol (compound 10 where === is a single bond), dehydroequol (compound 10 where === is a double bond), tetrahydrodaidzein (compound 8), and O-desmethyl-angolensin (ODMA).

20. A method according to claim 3 wherein the compounds of Formula (I) are genistein, equol (compound 10 where === is a single bond), dehydroequol (compound 10 where === is a double bond), tetrahydrodaidzein (compound 8), and O-desmethyl-angolensin (ODMA).

21. A method according to claim 4 wherein the compounds of Formula (I) are genistein, equol (compound 10 where === is a single bond), dehydroequol (compound 10 where === is a double bond), tetrahydrodaidzein (compound 8), and O-desmethyl-angolensin (ODMA).

* * * * *

UNITED STATES PATENT AND TRADEMARK OFFICE
CERTIFICATE OF CORRECTION

PATENT NO. : 6,455,032 B1
APPLICATION NO. : 09/582317
DATED : September 24, 2002
INVENTOR(S) : Graham Edmund Kelly et al.

It is certified that error appears in the above-identified patent and that said Letters Patent is hereby corrected as shown below:

Column 3
Line 35, the structure

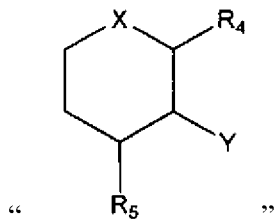

should read as

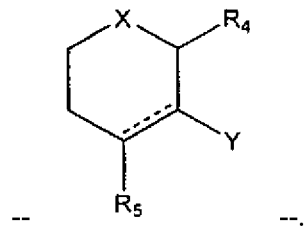

" -- --.

Column 5
Line 55, the structure

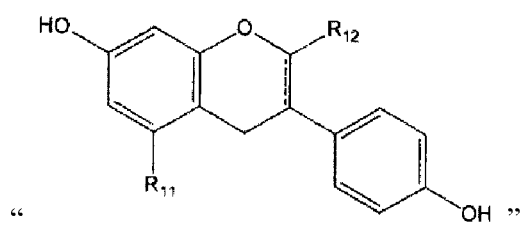

should read as

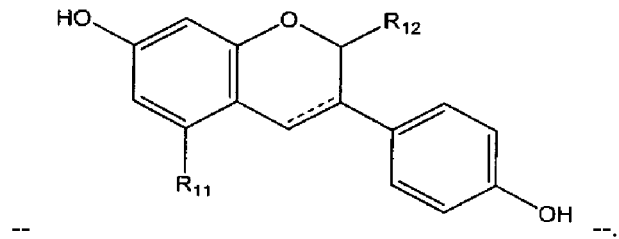

" -- --.

Column 15
Line 35, the structure

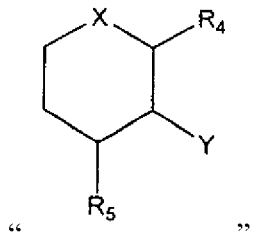

should read as

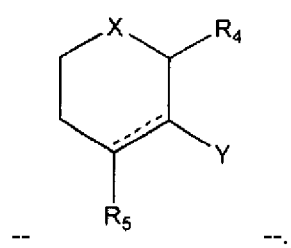

" -- --.

Signed and Sealed this
Eighth Day of May, 2012

David J. Kappos
*Director of the United States Patent and Trademark Office*

CERTIFICATE OF CORRECTION (continued)
U.S. Pat. No. 6,455,032 B1

Column 17
Line 40, the structure

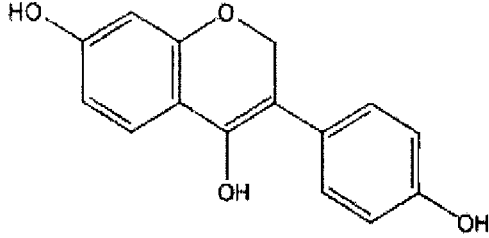
"

should read as

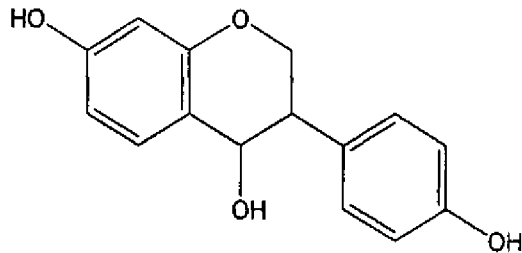
--.

Column 17
Line 55, the structure

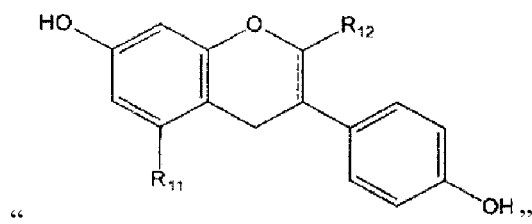
"

should read as

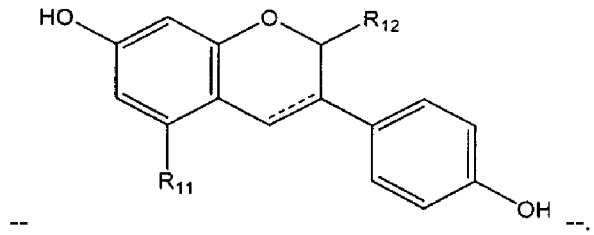
--.

Column 18
Line 17, the structure

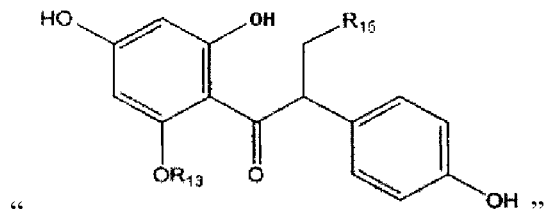
"

should read as

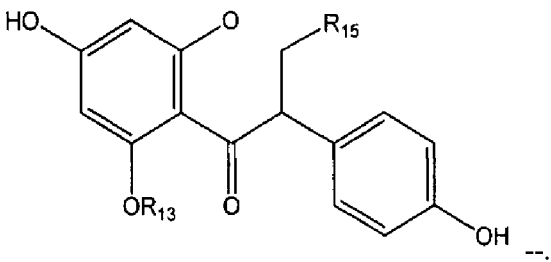
--.